US012409243B2

(12) United States Patent
Hu

(10) Patent No.: US 12,409,243 B2
(45) Date of Patent: *Sep. 9, 2025

(54) ANTI-ODOR COMPOSITIONS, STRUCTURES HAVING ANTI-ODOR CHARACTERISTICS, METHODS OF MAKING THE ANTI-ODOR COMPOSITIONS AND THE STRUCTURES

(71) Applicant: NIKE, Inc., Beaverton, OR (US)

(72) Inventor: Cheng Hu, Lake Oswego, OR (US)

(73) Assignee: Nike, Inc., Beaverton, OR (US)

( * ) Notice: Subject to any disclaimer, the term of this patent is extended or adjusted under 35 U.S.C. 154(b) by 238 days.

This patent is subject to a terminal disclaimer.

(21) Appl. No.: 17/398,413

(22) Filed: Aug. 10, 2021

(65) Prior Publication Data
US 2021/0361805 A1 Nov. 25, 2021

Related U.S. Application Data

(60) Continuation of application No. 16/590,710, filed on Oct. 2, 2019, now Pat. No. 11,116,860, which is a division of application No. 15/895,487, filed on Feb. 13, 2018, now Pat. No. 10,471,164.

(60) Provisional application No. 62/458,632, filed on Feb. 14, 2017, provisional application No. 62/458,616, filed on Feb. 14, 2017.

(51) Int. Cl.
| | | |
|---|---|---|
| A61L 2/18 | (2006.01) | |
| D06M 11/70 | (2006.01) | |
| D06M 13/148 | (2006.01) | |
| D06M 13/17 | (2006.01) | |
| D06M 13/203 | (2006.01) | |
| D06M 15/03 | (2006.01) | |
| D06M 15/263 | (2006.01) | |
| D06M 15/27 | (2006.01) | |
| D06M 101/32 | (2006.01) | |
| D06M 101/38 | (2006.01) | |

(52) U.S. Cl.
CPC .............. A61L 2/18 (2013.01); D06M 11/70 (2013.01); D06M 13/148 (2013.01); D06M 13/17 (2013.01); D06M 13/203 (2013.01); D06M 15/03 (2013.01); D06M 15/263 (2013.01); D06M 15/27 (2013.01); A61L 2202/26 (2013.01); D06M 2101/32 (2013.01); D06M 2101/38 (2013.01); D10B 2501/043 (2013.01)

(58) Field of Classification Search
CPC ...... A61L 2/18; A61L 2202/26; D06M 11/70; D06M 13/148; D06M 13/17; D06M 13/203; D06M 15/03; D06M 15/263; D06M 15/27; D06M 2101/32; D06M 2101/38; D06M 13/11; D06M 15/53; D06M 16/00; D10B 2501/043
See application file for complete search history.

(56) References Cited

U.S. PATENT DOCUMENTS

| | | |
|---|---|---|
| 2,345,533 A | 3/1944 | Witt |
| 2,607,130 A | 8/1952 | Pearson |
| 2,929,803 A | 3/1960 | Henry et al. |
| 3,011,383 A | 12/1961 | Sylvester et al. |
| 3,060,513 A | 10/1962 | Klink et al. |
| 4,231,369 A | 11/1980 | Sorensen et al. |
| 4,705,356 A | 11/1987 | Berning et al. |
| 5,269,995 A | 12/1993 | Ramanathan et al. |
| 5,346,934 A | 9/1994 | Chriss |
| 5,500,067 A | 3/1996 | Jenkner |
| 5,572,817 A | 11/1996 | Chien |
| 5,628,128 A | 5/1997 | Miller et al. |
| 5,671,495 A | 9/1997 | Chen |
| 5,722,322 A | 3/1998 | Watanabe |
| 5,813,148 A | 9/1998 | Guerra |
| 5,815,950 A | 10/1998 | Wang |
| 5,928,456 A | 7/1999 | Souparis |
| 5,930,921 A | 8/1999 | Sorofman et al. |
| 5,979,078 A | 11/1999 | McLaughlin |
| 6,127,026 A | 10/2000 | Bonk et al. |
| 6,147,726 A | 11/2000 | Kubota et al. |
| 6,157,489 A | 12/2000 | Bradley, Jr. et al. |
| 6,164,777 A | 12/2000 | Li et al. |
| 6,402,879 B1 | 6/2002 | Tawney et al. |
| 6,497,862 B2 | 12/2002 | Oku et al. |
| 6,551,531 B1 | 4/2003 | Ford et al. |

(Continued)

FOREIGN PATENT DOCUMENTS

| | | |
|---|---|---|
| AU | 2007200128 A1 | 8/2007 |
| CH | 702116 B1 | 5/2011 |
| CN | 1309688 A | 8/2001 |
| CN | 1324222 A | 11/2001 |
| CN | 1799857 | 7/2006 |
| CN | 101356245 A | 1/2009 |
| CN | 101381903 A | 3/2009 |
| CN | 101396884 A | 4/2009 |
| CN | 101633786 A | 1/2010 |
| CN | 101666886 A | 3/2010 |
| CN | 101781860 A | 7/2010 |

(Continued)

OTHER PUBLICATIONS

Eladwi et al., "Unusual Draping Fashionable Designs Using Anti-Odor Finishing of Dyed/Printed Synthetic Fabrics" International Design Journal, Jan. 1, 2015, vol. 5, Issue 1, pp. 43-50. (Year: 2015).*

(Continued)

Primary Examiner — Aradhana Sasan
(74) Attorney, Agent, or Firm — Shook, Hardy & Bacon L.L.P.

(57) ABSTRACT

One or more aspects of the present disclosure are directed to aqueous solutions that can be used to make substrates such as an article that can inhibit or limit one or more sources of odor. In an aspect, the aqueous solution can include one or more components, where one of the components is an inhibiting agent that can function to inhibit or limit the sources of odor in an article such as a textile.

21 Claims, 5 Drawing Sheets

(56) References Cited

U.S. PATENT DOCUMENTS

| | | |
|---|---|---|
| 6,579,837 B1 | 6/2003 | Fleury et al. |
| 6,689,378 B1 | 2/2004 | Sun et al. |
| 6,761,959 B1 | 7/2004 | Bonkowski et al. |
| 7,006,294 B2 | 2/2006 | Steenblik et al. |
| 7,385,101 B2 | 6/2008 | Chandra et al. |
| 7,800,814 B2 | 9/2010 | Nishimura et al. |
| 7,848,008 B2 | 12/2010 | Nishimura et al. |
| 7,903,339 B2 | 3/2011 | Banerjee et al. |
| 7,955,695 B2 | 6/2011 | Argoitia |
| 8,264,637 B2 | 9/2012 | Cho et al. |
| 8,322,636 B2 | 12/2012 | Wu et al. |
| 8,339,597 B2 | 12/2012 | Dal Negro et al. |
| 8,408,470 B2 | 4/2013 | Komatsu et al. |
| 8,486,494 B2 | 7/2013 | Fukazawa et al. |
| 8,558,137 B2 | 10/2013 | Yuasa et al. |
| 8,685,185 B2 | 4/2014 | Guo et al. |
| 8,889,234 B2 | 11/2014 | Kwon et al. |
| 9,102,195 B2 | 8/2015 | Raksha et al. |
| 9,134,468 B2 | 9/2015 | Noizet et al. |
| 9,185,947 B2 | 11/2015 | Spencer et al. |
| 9,220,951 B1 | 12/2015 | Comeau |
| 9,279,771 B2 | 3/2016 | Aizenberg et al. |
| 9,527,340 B2 | 12/2016 | Szumski et al. |
| 9,557,457 B2 | 1/2017 | Gocho et al. |
| 10,048,411 B2 | 8/2018 | Parker |
| 10,471,164 B2 | 11/2019 | Hu |
| 10,649,113 B2 | 5/2020 | Bee et al. |
| 10,779,617 B2 | 9/2020 | Iovu |
| 10,928,553 B2 | 2/2021 | Bee et al. |
| 2001/0028921 A1 | 10/2001 | Shaw et al. |
| 2001/0031249 A1 | 10/2001 | Oku et al. |
| 2001/0042321 A1 | 11/2001 | Tawney et al. |
| 2001/0053454 A1 | 12/2001 | Higashi et al. |
| 2002/0150629 A1 | 10/2002 | Nishimura et al. |
| 2002/0183133 A1 | 12/2002 | Sano |
| 2002/0191234 A1 | 12/2002 | Ishimoto et al. |
| 2003/0074808 A1 | 4/2003 | Weaver et al. |
| 2003/0086030 A1 | 5/2003 | Taniguchi et al. |
| 2003/0191044 A1* | 10/2003 | Carswell ............... D06M 15/21 510/475 |
| 2004/0112252 A1 | 6/2004 | Zimmermann et al. |
| 2004/0142185 A1 | 7/2004 | Takushima |
| 2004/0156886 A1 | 8/2004 | Kose |
| 2004/0169928 A1 | 9/2004 | Nilsen et al. |
| 2004/0172855 A1 | 9/2004 | Aslanides |
| 2005/0031816 A1 | 2/2005 | Chang et al. |
| 2005/0056954 A1 | 3/2005 | Devlin et al. |
| 2005/0063067 A1 | 3/2005 | Phillips et al. |
| 2005/0211114 A1 | 9/2005 | Fahrenbach et al. |
| 2005/0238610 A1 | 10/2005 | Nielsen et al. |
| 2005/0260369 A1 | 11/2005 | Graf et al. |
| 2006/0023327 A1 | 2/2006 | Coombs et al. |
| 2006/0112599 A1 | 6/2006 | Braynock et al. |
| 2006/0128823 A1 | 6/2006 | Tsuchimura et al. |
| 2006/0270553 A1 | 11/2006 | Mori |
| 2007/0008439 A1 | 1/2007 | Nakayama et al. |
| 2007/0058260 A1 | 3/2007 | Steenblik et al. |
| 2007/0076069 A1 | 4/2007 | Edwards et al. |
| 2007/0105745 A1 | 5/2007 | Lawshe et al. |
| 2008/0040951 A1 | 2/2008 | Kates |
| 2008/0066347 A1 | 3/2008 | Suzuki |
| 2008/0248281 A1 | 10/2008 | Nakaguma et al. |
| 2008/0274359 A1 | 11/2008 | Lawrence et al. |
| 2008/0300359 A1 | 12/2008 | Hoshi et al. |
| 2008/0318004 A1 | 12/2008 | Ruehe et al. |
| 2009/0174944 A1 | 7/2009 | Yuasa et al. |
| 2009/0301649 A1 | 12/2009 | Augsberg et al. |
| 2010/0024597 A1 | 2/2010 | Dover et al. |
| 2010/0104810 A1 | 4/2010 | Fukazawa et al. |
| 2010/0152065 A1 | 6/2010 | Nishimura et al. |
| 2010/0199406 A1 | 8/2010 | Dua et al. |
| 2010/0199520 A1 | 8/2010 | Dua et al. |
| 2010/0222442 A1 | 9/2010 | Prissok et al. |
| 2010/0254007 A1 | 10/2010 | Toda |
| 2010/0266946 A1 | 10/2010 | Shirai et al. |
| 2010/0290109 A1 | 11/2010 | Kurt et al. |
| 2010/0291358 A1 | 11/2010 | Takahashi et al. |
| 2011/0026208 A1 | 2/2011 | Utsuro et al. |
| 2011/0033670 A1 | 2/2011 | Nishikawa et al. |
| 2011/0043911 A1 | 2/2011 | Kaneiwa et al. |
| 2011/0090564 A1 | 4/2011 | Utsuro et al. |
| 2011/0123754 A1 | 5/2011 | Shirai et al. |
| 2011/0171440 A1 | 7/2011 | Cheng et al. |
| 2011/0183111 A1 | 7/2011 | Yuasa et al. |
| 2011/0234953 A1 | 9/2011 | Amimori et al. |
| 2011/0234969 A1 | 9/2011 | Amimori et al. |
| 2011/0253288 A1 | 10/2011 | Xie et al. |
| 2011/0262675 A1 | 10/2011 | Inamiya et al. |
| 2011/0298207 A1 | 12/2011 | Despland et al. |
| 2012/0015118 A1 | 1/2012 | Zheludev et al. |
| 2012/0015145 A1 | 1/2012 | Depres |
| 2012/0034291 A1 | 2/2012 | Amsden et al. |
| 2012/0121820 A1 | 5/2012 | Cronin-Golomb et al. |
| 2012/0133672 A1 | 5/2012 | Joo |
| 2012/0139230 A1 | 6/2012 | Whiteman et al. |
| 2012/0204443 A1 | 8/2012 | Vertuccio |
| 2012/0231489 A1 | 9/2012 | Lenhert |
| 2012/0236415 A1 | 9/2012 | Nagano et al. |
| 2012/0249718 A1 | 10/2012 | Sohn et al. |
| 2012/0255201 A1 | 10/2012 | Little |
| 2012/0255452 A1 | 10/2012 | Bower et al. |
| 2012/0276332 A1 | 11/2012 | Conolly et al. |
| 2012/0297642 A1 | 11/2012 | Schaefer et al. |
| 2013/0004721 A1 | 1/2013 | Hara et al. |
| 2013/0004722 A1 | 1/2013 | Hara et al. |
| 2013/0004731 A1 | 1/2013 | Hara et al. |
| 2013/0004754 A1 | 1/2013 | Hara et al. |
| 2013/0148221 A1 | 6/2013 | Banerjee et al. |
| 2013/0183487 A1 | 7/2013 | Henze et al. |
| 2013/0243693 A1 | 9/2013 | Omenetto et al. |
| 2013/0330710 A1 | 12/2013 | Amsden et al. |
| 2014/0016177 A1 | 1/2014 | Aizenberg et al. |
| 2014/0050899 A1 | 2/2014 | Kukoff |
| 2014/0104686 A1 | 4/2014 | Yuasa et al. |
| 2014/0106139 A1 | 4/2014 | Abrams |
| 2014/0161974 A1 | 6/2014 | Erho et al. |
| 2014/0182169 A1 | 7/2014 | Mack |
| 2014/0250734 A1 | 9/2014 | Zheng |
| 2014/0254017 A1 | 9/2014 | Manoharan et al. |
| 2015/0001840 A1 | 1/2015 | Parker |
| 2015/0035269 A1 | 2/2015 | Hooper et al. |
| 2015/0076808 A1 | 3/2015 | Kim et al. |
| 2015/0109657 A1 | 4/2015 | Baumberg et al. |
| 2015/0118124 A1 | 4/2015 | Khorasaninejad et al. |
| 2015/0146280 A1 | 5/2015 | Degott et al. |
| 2015/0179357 A1 | 6/2015 | Ichinomiya et al. |
| 2015/0192897 A1 | 7/2015 | Schilling et al. |
| 2015/0202834 A1 | 7/2015 | Free et al. |
| 2015/0250263 A1 | 9/2015 | Robinson, Jr. |
| 2015/0283743 A1 | 10/2015 | Park et al. |
| 2015/0309232 A1 | 10/2015 | Banerjee |
| 2015/0352883 A1 | 12/2015 | Schmid et al. |
| 2015/0352888 A1 | 12/2015 | Schmid et al. |
| 2016/0064696 A1 | 3/2016 | Collier et al. |
| 2016/0101601 A1 | 4/2016 | Abrams |
| 2016/0116645 A1 | 4/2016 | Parker |
| 2016/0128433 A1 | 5/2016 | Downing et al. |
| 2016/0131808 A1 | 5/2016 | Kristensen et al. |
| 2016/0146984 A1 | 5/2016 | Jiang et al. |
| 2016/0168386 A1 | 6/2016 | Aizenberg et al. |
| 2016/0176223 A1 | 6/2016 | Degott et al. |
| 2016/0178493 A1 | 6/2016 | Kawanaka et al. |
| 2016/0202394 A1 | 7/2016 | Clausen et al. |
| 2016/0202401 A1 | 7/2016 | Christiansen et al. |
| 2016/0209642 A1 | 7/2016 | Aizenberg et al. |
| 2016/0282527 A1 | 9/2016 | Saito et al. |
| 2016/0324269 A1 | 11/2016 | Dombrow et al. |
| 2016/0325310 A1 | 11/2016 | Schmid et al. |
| 2017/0023711 A1 | 1/2017 | Jiang et al. |
| 2017/0081535 A1 | 3/2017 | Kohri et al. |
| 2017/0087691 A1 | 3/2017 | Yokoyama et al. |
| 2017/0090084 A1 | 3/2017 | Wilson et al. |
| 2017/0129200 A1 | 5/2017 | Adami et al. |
| 2017/0157653 A1 | 6/2017 | Parker |

(56) References Cited

U.S. PATENT DOCUMENTS

| | | | |
|---|---|---|---|
| 2017/0248746 A1 | 8/2017 | Banerjee et al. |
| 2017/0347745 A1 | 12/2017 | Figur et al. |
| 2018/0252158 A1 | 9/2018 | Malkamäki et al. |
| 2018/0257360 A1 | 9/2018 | Liponkoski |
| 2018/0284330 A1 | 10/2018 | Parker |
| 2018/0357316 A1 | 12/2018 | Neuvonen et al. |
| 2019/0098946 A1 | 4/2019 | Bee et al. |
| 2019/0098958 A1 | 4/2019 | Bee et al. |
| 2019/0099967 A1 | 4/2019 | Bee et al. |
| 2019/0099968 A1 | 4/2019 | Bee et al. |
| 2019/0099978 A1 | 4/2019 | Bee et al. |
| 2019/0099979 A1 | 4/2019 | Bee et al. |
| 2019/0113655 A1 | 4/2019 | Bee et al. |
| 2019/0113656 A1 | 4/2019 | Bee et al. |
| 2020/0040882 A1 | 2/2020 | Kalmari et al. |
| 2020/0088908 A1 | 3/2020 | Bee et al. |
| 2020/0181550 A1 | 6/2020 | Kalmari et al. |
| 2020/0217986 A1 | 7/2020 | Bee et al. |
| 2020/0217987 A1 | 7/2020 | Bee et al. |
| 2020/0240667 A1 | 7/2020 | Lind |
| 2020/0269561 A1 | 8/2020 | Bee et al. |
| 2020/0275728 A1 | 9/2020 | Bee et al. |
| 2020/0305526 A1 | 10/2020 | Gantz et al. |
| 2020/0305527 A1 | 10/2020 | Gantz et al. |
| 2020/0308734 A1 | 10/2020 | Gantz et al. |
| 2020/0314185 A1 | 10/2020 | Mäkynen et al. |
| 2020/0371272 A1 | 11/2020 | Bee et al. |
| 2020/0407838 A1 | 12/2020 | Gantz et al. |

FOREIGN PATENT DOCUMENTS

| | | | | |
|---|---|---|---|---|
| CN | 102548752 A1 | 7/2012 | | |
| CN | 102691202 A | 9/2012 | | |
| CN | 103173039 A | 6/2013 | | |
| CN | 103893804 A | 7/2014 | | |
| CN | 103965699 A | 8/2014 | | |
| CN | 104334042 A | 2/2015 | | |
| CN | 104592971 A | 5/2015 | | |
| CN | 105050442 A | 11/2015 | | |
| CN | 105133296 A | 12/2015 | | |
| CN | 105220483 A | 1/2016 | | |
| CN | 105267048 A | 1/2016 | | |
| CN | 105271796 A | 1/2016 | | |
| CN | 105862000 A | 8/2016 | | |
| CN | 106080001 A | 11/2016 | | |
| CN | 107111002 A | 8/2017 | | |
| DE | 20200346 U1 | 4/2002 | | |
| DE | 102010025159 A1 | 12/2011 | | |
| EP | 0335309 A1 | 10/1989 | | |
| EP | 0905530 A2 | 3/1999 | | |
| EP | 1129693 A2 | 9/2001 | | |
| EP | 1624026 A1 | 2/2006 | | |
| EP | 1653256 A1 | 5/2006 | | |
| EP | 2012148 A1 | 1/2009 | | |
| EP | 2077459 A1 | 7/2009 | | |
| EP | 2508922 A1 | 10/2012 | | |
| EP | 3061865 A | 8/2016 | | |
| EP | 3151042 A1 | 4/2017 | | |
| EP | 3244240 A1 | 11/2017 | | |
| EP | 3278150 A1 | 2/2018 | | |
| GB | 2374818 A | 10/2002 | | |
| GB | 2481697 A | 1/2012 | | |
| GB | 2524840 A | 10/2015 | | |
| GB | 2525020 A | 10/2015 | | |
| JP | S601180 U | 1/1985 | | |
| JP | 2005226196 A | 8/2005 | | |
| JP | 2006288907 A | 10/2006 | | |
| JP | 2009211077 A | 9/2009 | | |
| JP | 2010111974 A | 5/2010 | | |
| JP | 2010132634 A | 6/2010 | | |
| JP | 2011085779 A | 4/2011 | | |
| JP | 2011104931 A | 6/2011 | | |
| JP | 2012159589 A | 8/2012 | | |
| JP | 2013029805 A | 2/2013 | | |
| JP | 2013080049 A | 5/2013 | | |
| JP | 2014189719 A | 10/2014 | | |
| JP | 2015069076 A | 4/2015 | | |
| JP | 2016502470 A | 1/2016 | | |
| JP | 2017032409 A | 2/2017 | | |
| KR | 101472929 B1 | 12/2014 | | |
| TW | I230076 B | 4/2005 | | |
| TW | 200628089 A | 8/2006 | | |
| WO | 9701972 A1 | 1/1997 | | |
| WO | WO-0024851 A2 * | 5/2000 | ........... | C11D 17/041 |
| WO | 2003046039 A1 | 6/2003 | | |
| WO | 03068525 A1 | 8/2003 | | |
| WO | 3095657 A2 | 11/2003 | | |
| WO | 2007037393 A1 | 4/2007 | | |
| WO | 2007038097 A1 | 4/2007 | | |
| WO | 2008076339 A2 | 6/2008 | | |
| WO | 2009062341 A1 | 5/2009 | | |
| WO | 2010047322 A1 | 4/2010 | | |
| WO | 2010119248 A2 | 10/2010 | | |
| WO | 2011161482 A1 | 12/2011 | | |
| WO | 2012055105 A1 | 5/2012 | | |
| WO | 2013151547 A1 | 10/2013 | | |
| WO | 2014022049 A1 | 2/2014 | | |
| WO | 2014059424 A2 | 4/2014 | | |
| WO | 2014117673 A1 | 8/2014 | | |
| WO | 2014133514 A1 | 9/2014 | | |
| WO | 2015051367 A1 | 4/2015 | | |
| WO | 2015151479 A1 | 10/2015 | | |
| WO | 2015170120 A1 | 11/2015 | | |
| WO | 2016015973 A1 | 2/2016 | | |
| WO | 2016092014 A1 | 6/2016 | | |
| WO | 2016103980 A1 | 6/2016 | | |
| WO | 2016140779 A1 | 9/2016 | | |
| WO | 2016156863 A2 | 10/2016 | | |
| WO | 2016164551 A1 | 10/2016 | | |
| WO | 2016193252 A1 | 12/2016 | | |
| WO | 2017006314 A1 | 1/2017 | | |
| WO | 2017032928 A1 | 3/2017 | | |
| WO | 2017041085 A1 | 3/2017 | | |
| WO | 2017115806 A1 | 7/2017 | | |
| WO | 2017151496 A1 | 9/2017 | | |
| WO | 2018130856 A1 | 7/2018 | | |
| WO | 2018160866 A1 | 9/2018 | | |
| WO | 2019038560 A | 2/2019 | | |
| WO | 2019067969 A1 | 4/2019 | | |
| WO | 2019086770 A1 | 5/2019 | | |
| WO | 2019224426 A1 | 11/2019 | | |
| WO | 2020030844 A1 | 2/2020 | | |
| WO | 2020197774 A1 | 10/2020 | | |

OTHER PUBLICATIONS

Charbonnet et al., "New Approaches in Cotton Crosslinking—Green Team Final Report to Levi Strauss & Co." Greener Solutions 2013 University of California, Berkeley, pp. 1-71 (Year: 2013).*
Written Opinion and International Search Report for PCT/US2018/017987 mailed May 17, 2018.
International Preliminary Report on Patentability PCT/US2018/017987, mailed Jan. 24, 2019.

* cited by examiner

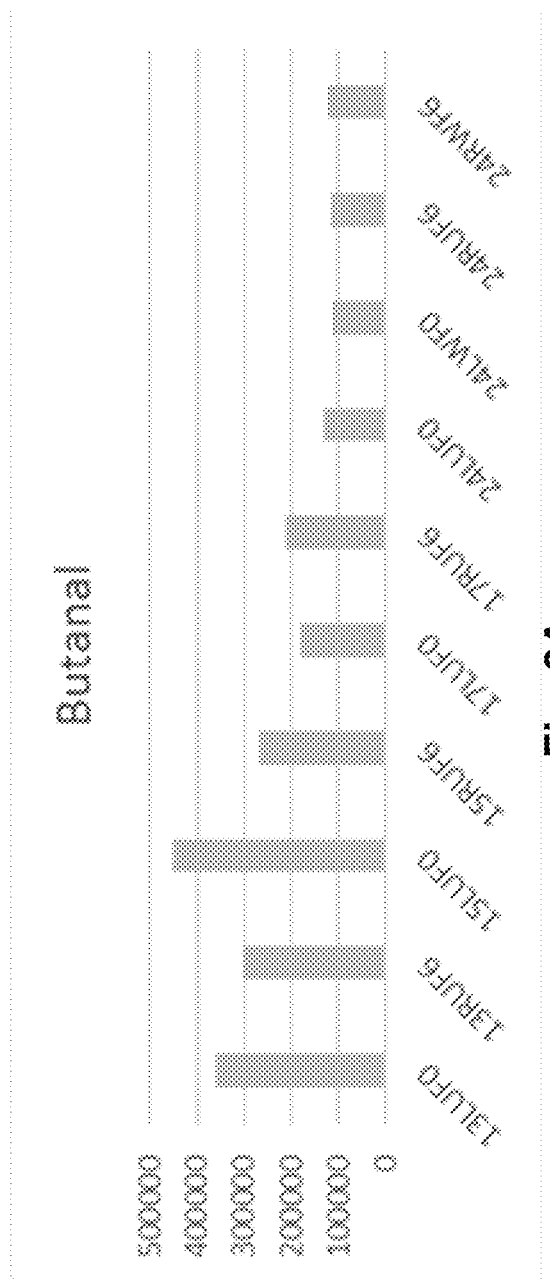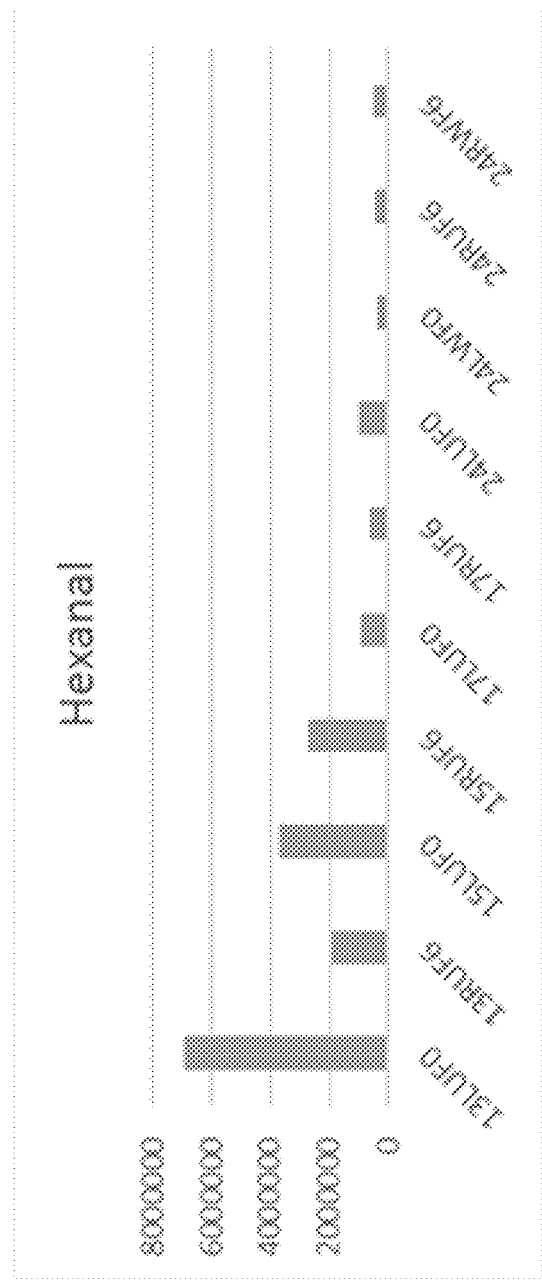

ANTI-ODOR COMPOSITIONS, STRUCTURES HAVING ANTI-ODOR CHARACTERISTICS, METHODS OF MAKING THE ANTI-ODOR COMPOSITIONS AND THE STRUCTURES

CROSS-REFERENCE TO RELATED APPLICATIONS

This application is a Continuation of and claims priority to U.S. Non-Provisional application Ser. No. 16/590,710, having the title "ANTI-ODOR COMPOSITIONS, STRUCTURES HAVING ANTI-ODOR CHARACTERISTICS, METHODS OF MAKING THE ANTI-ODOR COMPOSITIONS AND THE STRUCTURES", filed on Oct. 2, 2019, which claims the benefit of and priority to U.S. Non-Provisional application Ser. No. 15/895,487, having the title "ANTI-ODOR COMPOSITIONS, STRUCTURES HAVING ANTI-ODOR CHARACTERISTICS, METHODS OF MAKING THE ANTI-ODOR COMPOSITIONS AND THE STRUCTURES", filed on Feb. 13, 2018; claims the benefit of and priority to U.S. Provisional Application Ser. No. 62/458,616, having the title "ANTI-ODOR COMPOSITIONS, STRUCTURES HAVING ANTI-ODOR CHARACTERISTICS, METHODS OF MAKING THE ANTI-ODOR COMPOSITIONS AND THE STRUCTURES", filed on Feb. 14, 2017; and claims the benefit of and priority to U.S. Provisional Application Ser. No. 62/458,632, having the title "ANTI-ODOR COMPOSITIONS, STRUCTURES HAVING ANTI-ODOR CHARACTERISTICS, METHODS OF MAKING THE ANTI-ODOR COMPOSITIONS AND THE STRUCTURES", filed on Feb. 14, 2017, the disclosures of which are incorporated herein by reference in their entireties.

BACKGROUND

During exercise or strenuous effort, humans perspire and the perspiration is absorbed by the clothing. The components of the perspiration can be converted to malodorous compounds through chemical or biochemical mechanisms that can involve naturally present bacteria on the skin. In addition, compounds on the clothing can react during cleaning and cause odors that are difficult to remove from the clothing. There are many ways to address the odor and some include masking the odor with more pleasant smells, prevent the odor from being formed by wicking the perspiration from the skin, killing the bacteria that can produce the malodorous compounds, and the like. However, these efforts have not addressed all of the problems associated with odors and may cause other problems.

BRIEF DESCRIPTION OF THE DRAWINGS

Further aspects of the present disclosure will be more readily appreciated upon review of the detailed description of its various embodiments, described below, when taken in conjunction with the accompanying drawings.

FIGS. 2A-G illustrates graphs of gas chromatograph/gas chromatograph-time of flight mass spectrometry (GC/GC-TOFMS) profiling of aldehyde compounds on worn fabric samples.

Figure 1:
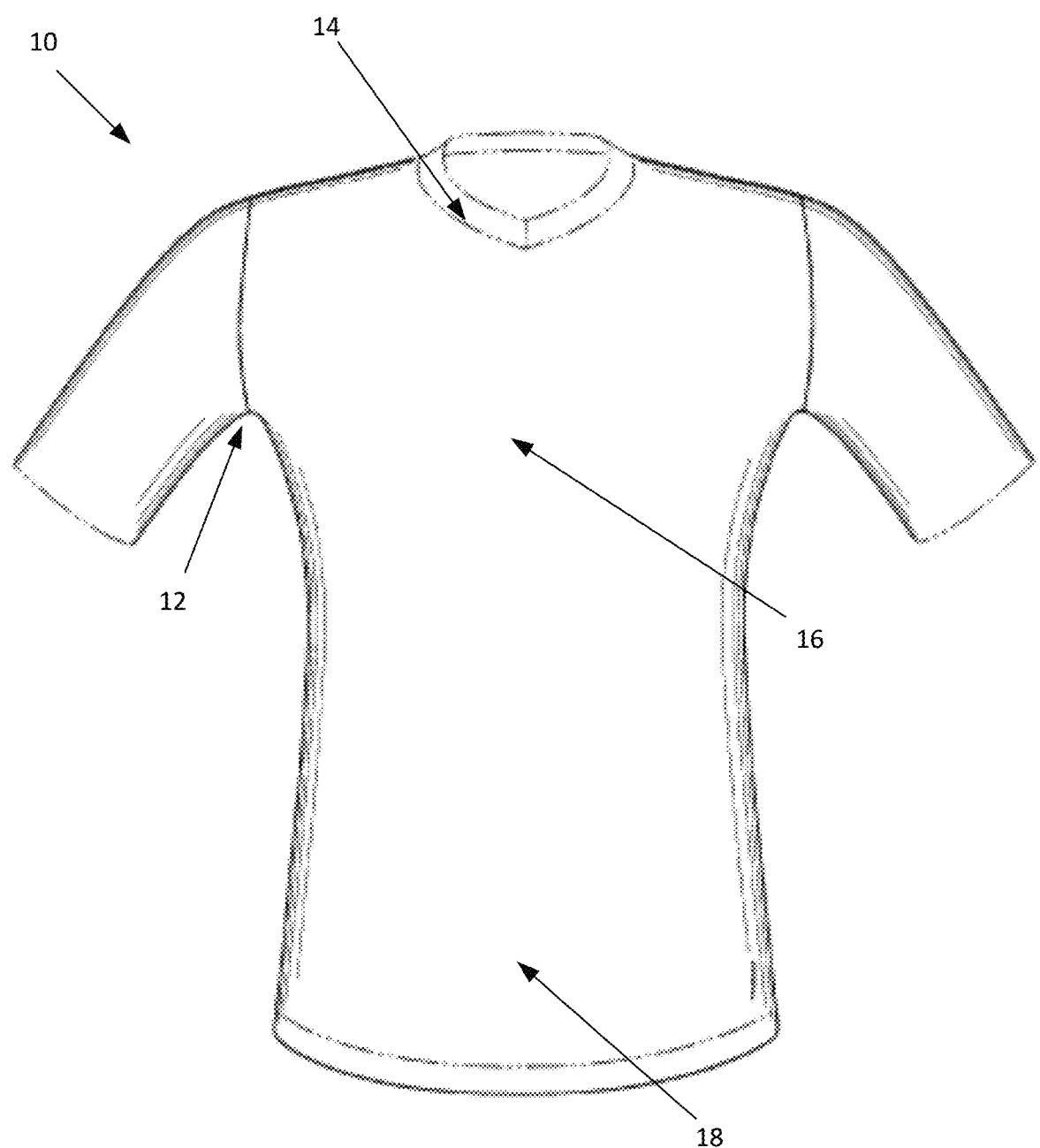
FIG. 1 is an example of an article of apparel with anti-odor characteristics.

The drawings illustrate only example embodiments and are therefore not to be considered limiting of the scope described herein, as other equally effective embodiments are within the scope and spirit of this disclosure.

DETAILED DESCRIPTION

One or more aspects of the present disclosure are directed to aqueous solutions that can be used to make substrates such as an article that can inhibit or limit one or more sources of odor. In an aspect, the aqueous solution can include one or more components, where one of the components is an inhibiting agent that can function to inhibit or limit the sources of odor in an article such as a textile. In a particular aspect, the inhibiting agent can function as a lipid peroxidation inhibitor, an aldehyde inhibitor, and/or an antioxidant. The solution can also include one or more additional components such as: a stain release agent, a cross-linker, a softener, and an alkali metal salt catalyst. The substrate can be manufactured by exposing the aqueous solution to an untreated substrate to form a surface coating on the article and the article has the characteristic of inhibiting or limiting the sources of odor. In an aspect, the substrate can be an assembled article such as a shirt or can be a part of an article that is subsequently cut and assembled into an article. An example of a substrate includes a textile article, fully assembled or uncut and unassembled, including polyester (e.g., polyethylene terephthalate (PET)), and it is known that textiles including polyester (e.g., PET) retain odor more than other textiles. In this regard, the textile including polyester can be treated (before or after assembly) with the aqueous solution to form a surface coating on the textile and the treated textile has the characteristic of retaining less odor than textiles that are not treated with the aqueous solution.

In an aspect, the present disclosure provides for an aqueous solution comprising: an inhibitor agent and, optionally, one or more of the following: a cross-linker, a softener, and an alkali metal salt catalyst, wherein the inhibitor agent functions in one or more of the following ways: as a lipid peroxidation inhibitor, as an aldehyde inhibitor, or as an antioxidant, and wherein the concentration of the inhibitor agent is about 0.01 to less than 10 wt % of the solution.

In an aspect, the present disclosure provides for an aqueous solution comprising: aqueous solution comprising: a trehalose at about 0.01 to 10 weight % of the solution and one or more of the following: polyacrylic acid at about 0.01 to 5 weight % of the solution; sodium hypophosphite at about 0.01 to 10 weight % of the solution; and polyethylene glycol ester at about 0.01 to 6 weight % of the solution.

Another aspect of the present disclosure includes methods of treating a substrate (e.g., textile, polyesters) that includes exposing the substrate to the aqueous solution as described above or herein; drying the substrate; and curing the substrate to form a treated substrate.

An aspect of the present disclosure includes an article, comprising: a treated substrate having a surface coating comprising an inhibitor agent. Another aspect of the present disclosure includes substrate, comprising: a treated substrate having a surface coating comprising trehalose and one or more of the following: polyacrylic acid, sodium hypophosphite, and polyethylene glycol ester.

Now having describe aspect of the present disclosure generally, additional discussion regarding aspects will be described in greater detail.

This disclosure is not limited to particular aspects described, and as such may, of course, vary. The terminology used herein serves the purpose of describing particular aspects only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual aspects described and illustrated herein has discrete components and features which may be readily separated from or combined with the features of any of the other several aspects without departing from the scope or spirit of the present disclosure. Any recited method may be carried out in the order of events recited or in any other order that is logically possible.

Aspects of the present disclosure will employ, unless otherwise indicated, techniques of material science, chemistry, textiles, polymer chemistry, and the like, which are within the skill of the art. Such techniques are explained fully in the literature.

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As described above, one or more aspects of the present disclosure provide aqueous solutions that can be used to make a surface coating or layer on a treated structure (e.g., a treated textile), where the surface coating has the characteristic of inhibiting or limiting one or more sources of odor. As used herein, "odor" refers to unpleasant or disagreeable smells associated with an article or textile. For example, the textile can have a malodorous smell as a result of activities (e.g., exercise, physical labor, strenuous activity, or the like) and/or residual smells after cleaning. Some materials such as polyesters retain odors more than other materials, so while these materials may provide comfort or other desirable characteristics, the odor associated with these materials is not desirable.

Odor can be formed in many ways and a number of mechanisms produce the malodorants. In short, the components in sweat (e.g., water, proteins, lipids (e.g., fatty acids), and other compounds), other skin secretions, or other bodily fluids can interact with bacteria naturally on the skin to break down these components to generate volatile malodorants compounds. The types of bacteria and the types of compounds that can be produced varies considerably, which makes addressing odor a complex problem.

The words "inhibit" or "inhibiting" do not mean that the source of odor must be inhibited 100%, rather the source of the odor can be reduced relative to an untreated substrate, article, or textile. For example, the amount of inhibition can include about 10% or more, about 15% or more, about 25% or more, about 30% or more, about 40% or more, about 50% or more, about 60% or more, about 70% or more, about 80% or more, about 90% or more, about 95% or more, about 99% or more, or about 100% inhibition relative to an untreated structure. In addition, the words "inhibit" or "inhibiting" mean reducing or hindering the ability of the odor sources (e.g., chemical and/or biological) to produce or generate (e.g., via bacteria), directly or indirectly, the odor, which may include the chemicals associated, directly or indirectly, with the odor. The chemical or biochemical process can be disrupted at one or more stages to reduce the amount of odor causing chemicals or prevent the process from even occurring.

In an aspect, the structure can be the article or be a part of the article. In an aspect the article can include a textile, where the textile can be a woven, non-woven, braided, or knit textile. In an aspect, the textile can include fibers, yarns, or fabrics made of natural (e.g., cotton, silk, wool, and the like) and/or synthetic fibers (e.g., polyesters, polyamides, polyolefins, and the like). The synthetic material can include polyesters, polyolefins, halogenated polymers, polyamides, polyurethanes, polyaramids, as well as homopolymers, copolymers, or terepolymers in any combination of these.

In aspects, the textile can be made of one or more elements, where multiple elements can be sewed, welded, or otherwise associated to or with one another to form the textile. In an aspect, the textile can be treated with the aqueous solution at any stage of manufacture or use (e.g. during textile manufacture, to a manufactured textile or article, to elements of an article before assembly of an article, after assembly of an article, device, or apparel item). In another aspect, the fibers, yarns, or fabrics can be treated prior to making the part of the article.

In an aspect, the textile can include footwear, apparel (e.g., shirts, jerseys, pants, shorts, gloves, glasses, socks, hats, caps, jackets, undergarments), containers (e.g., backpacks, bags), and upholstery for furniture (e.g., chairs, couches, car seats), or bed coverings (e.g., sheets, blankets). In addition, the structure can be used with or disposed on articles, textiles or other items such as striking devices (e.g., bats, rackets, sticks, mallets, golf clubs, paddles, etc.), athletic equipment (e.g., golf bags, baseball and football gloves), protective equipment (e.g., pads, helmets, guards, visors, masks, goggles, etc.), or other items that come into contact with human skin, or component of any of the foregoing, where each of these can be referred to as a product. FIG. 1 illustrates a shirt 10, where one or more areas (e.g., 12, 14, 16, 18) of the shirt 10 can include a treated area with the aqueous solution.

In an aspect, the aqueous solution includes an inhibitor agent. The concentration of the inhibitor agent can be about 0.01 to about 15 wt % of the solution, about 0.01 to about 10 wt % of the solution, about 0.01 to about 5 wt % of the solution, about 0.01 to less than about 5 wt % of the solution, about 0.01 to less than 5 wt % of the solution (in this phrase "less than 5 wt %" does not include "less than about 5 wt %"), about 0.01 to about 4 wt % of the solution, about 0.01 to about 2 wt % of the solution, or about 0.01 to about 1 wt % of the solution. In each of the ranges above for the inhibitor agent, the lower range can also be any one of about 0.1, about 0.5, about 1, and about 2.

In an aspect, the inhibitor agent can function to disrupt or prevent one or more steps of one or more mechanisms that produce malodorants. The inhibitor agent can function in one or more of the following ways: as a lipid peroxidation inhibitor, as an aldehyde inhibitor, or as an antioxidant. Lipid peroxidation inhibition includes disrupting or preventing the oxidation of lipids (e.g. those excreted from the skin), which may include disrupting or preventing one or more steps in the mechanism for oxidizing lipids. Aldehyde inhibition includes disrupting or preventing the formation of aldehydes, which may include disrupting or preventing one or more steps in the mechanism for forming aldehydes. The antioxidant can disrupt or prevent the oxidation of compounds that can be made into malodorants, which may include disrupting or preventing one or more steps in the oxidation mechanism.

In an aspect, the inhibitor agent can include a polysaccharide, an antioxidant, L-ascorbic acid, or a modified antioxidative antimicrobial chitosan. The polysaccharide can include trehalose or a trehalose derivative, where the derivative can include substitution of one or more H with a halogen or C1-C4 alkyl group.

In an aspect, the inhibitor agent can be trehalose. The concentration of the trehalose can be about 0.01 to about 15 wt % of the solution, about 0.01 to about 10 wt % of the solution, about 0.01 to about 5 wt % of the solution, about 0.01 to less than about 5 wt % of the solution, about 0.01 to less than 5 wt % of the solution (in this phrase "less than 5 wt %" does not include "less than about 5 wt %"), about 0.01 to about 4 wt % of the solution, about 0.01 to about 2 wt % of the solution, or about 0.01 to about 1 wt % of the solution. In each of the ranges above for the inhibitor agent, the lower range can also be any one of about 0.1, about 0.5, about 1, and about 2.

In an aspect the aqueous solution can include one, two, or three of the following: a stain release agent, a cross-linker, a softener, and an alkali metal salt catalyst. In an aspect the aqueous solution can include each of the stain release agent, the cross-linker, the softener, and the alkali metal salt catalyst. In each aspect, one or more types of each of the stain release agent, the cross-linker, the softener, and/or the alkali metal salt catalyst can be present in the aqueous solution. In other words, the aqueous solution can include two or more types of cross-linkers, for example.

The stain release agent can function to reduce the ability of the treated substrate to stain and/or allow for the stain to be more easily removed from the substrate. In an aspect the stain release agent can include one or more of the following: a carboxymethyl cellulose salt, an oligomeric copolymers of terephthalic acid with ethylene glycol and polyethylene glycol, a carboxy based hydrophilic polymer, or a combination thereof. The concentration of the stain release agent can be about 0.01 to 5 weight % or about 0.5 to 5 weight % of the solution.

The cross-linker can function to cross-link one or more components of the aqueous solution with one another and/or with the substrate, for example, with the surface of textile. In an aspect, the cross-linker can include one or more of the following: a polycarboxylic acid crosslinking agent, an aldehyde crosslinking agent, a polyisocyanate crosslinking agent, or a combination thereof. The polycarboxylic acid crosslinking agent can be a $C_2$-$C_9$ polycarboxylic acid. For example, the cross-linker can include a polyacrylic acid, a polymaleic acid, a copolymer of acid, a copolymer of maleic acid, fumaric acid, or 1, 2, 3, 4-butanetetracarboxylic acid. The concentration of the cross-linker can be about 0.01 to 5 weight % or 1 to 3 weight % of the solution.

The alkali metal salt catalyst can function to catalyze the cross-linking reaction(s). In an aspect the alkali metal salt catalyst can be selected from: alkali metal hypophosphites, alkali metal phosphites, alkali metal polyphosphonates, alkali metal phosphates, and alkali metal sulfonates. The hypophosphorous salt can be sodium hypophosphite. The concentration of the alkali metal salt catalyst can be about 0.01 to 10 weight % or about 1 to 5 weight % of the solution.

The softener can function to give the substrate a softer feel relative to the substrate without the softener. The softener can comprise a silicone, a fatty acid derivative, an aliphatic glycol ester, an aliphatic phthalate copolymer, a derivative of an aliphatic phthalate copolymer, or any combination thereof. In some aspects, the softener is a hydrophilic softener (e.g., a softener which, when applied to a substrate, results in the surface of the softener-treated substrate having a lower water contact angle than the surface of the untreated substrate). In an aspect the softener can be a polyethylene glycol ester (e.g., a molecular weight of about 300 to 100,000) or a polyethylene glycol ester derivative. In an aspect the softener can be a polyethylene terephthalate copolymer, or derivatives of polyethylene terephthalate. The concentration of the softener can be about 0.01 to 6 weight % or about 1 to 3 weight % of the solution.

Now having described the aqueous solution, methods of using the aqueous solution and treated structure are now described. In an aspect, the method of treating the substrate includes exposing the substrate to the aqueous solution. The substrate can be exposed in a number of ways, such as dipping the substrate in the aqueous solution, foaming the aqueous solution onto the substrate, spraying the aqueous solution onto the substrate, combinations thereof, and the like. In an example, the substrate is a textile and known methods for introducing a solution to a textile can be used to introduce the aqueous solution to the textile.

After an appropriate amount of time (e.g., about 2 seconds to a minute or more) for the substrate to be exposed to the aqueous solution, the substrate and aqueous solution are separated from one another and the substrate is dried. In an example, the textile fabric can have a wet pickup of about 50 to 100 weight %. Wet pickup is a measure of the amount of liquid taken up by a substrate when the substrate is dipped into the liquid. Commonly, a substrate is weighted when dry and then dipped into a bath of the liquid, run through a series of rollers to wring excess liquid from the substrate, and re-weighed to determine its wet weight. As used herein, the weight percent of wet pickup is determined by subtracting the dry weight of the substrate from the wet weight of the substrate, dividing that value by the dry weight of the substrate, and then multiplying that value by 100.

The substrate is then cured (e.g., the substrate is heated to a temperature of about 120 to 160° C. for 30 seconds to 5 minutes or more) to form the treated substrate that includes a surface coating. In an example, the substrate is a textile fabric and the surface coating is on the fabric. Although not intending to be bound by theory, components of the aqueous solution and/or the substrate cross-link to form the surface coating. For example, the inhibitor agent, the cross-linker and/or the stain release agent, can cross-link with one another and/or with the terminal groups of the substrate. In an aspect, trehalose, polyacrylic acid, and/or carboxymethyl cellulose, can cross-link with one another and/or with the terminal groups of the substrate such as a PET substrate.

The surface coating can be about 10 nm to 10,000 µm. In an aspect, the surface coating can be applied so that it is uniformly distributed throughout the thickness of a fabric (e.g., on and among the fibers, yarns, fabric, etc.). In another aspect, the surface coating can be applied so that it is applied to select portions of the fabric (e.g., areas, sides, and the like) to achieve the desired odor reducing characteristics. In an aspect, the treated substrate can include a product of the methods described herein.

In an aspect, the treated substrate can include a surface coating that includes the inhibitor agent (e.g., trehalose) or compounds incorporating the inhibitor agent in a way that the inhibitor agent functions to inhibit odor. In an aspect, the inhibitor agent can be covalently bonded to a polymer that is attached to the substrate, such as the fabric of a textile. In addition or in the alternative, the inhibitor agent can be non-covalently incorporated into the substrate such as the fabric of a textile.

In an aspect, the surface coating may not cover all surfaces of the substrate and portions of the substrate may be free of the surface coating. In another aspect, the surface coating may cover a large portion of the substrate, for example, the substrate is a fabric of a textile and the fabric contacting the skin is coated or the surface coating is on portions of the fabric that contact specific areas of the individual (e.g., under arms area, groin area, and the like). In another aspect, the surface coating may cover all of the substrate, for example all surfaces of a textile shirt.

In an aspect, one or more other components can be included in the surface coating such as the stain release agent, the cross-linker, the softener, and the alkali metal salt catalyst. Similarly to the inhibitor agent, each of these components are present in the surface coating or are incorporated in the surface coating in a way that the each functions as they are intended. The surface coating can include one or more cross-linked groups that incorporate one or more of the components. The alkali metal salt catalyst may or may not be present in the surface coating since this component is used to catalyze the cross-linking reactions.

As stated above, the substrate, or precursor materials (e.g., fibers, yarn, etc.), can be treated with the aqueous solution. The treatment can be at any stage of manufacture and the treatment can be for the entire substrate or for individual elements used to make the substrate. For example, one or more areas of the textile to form the textile can be treated during manufacture of the textile, during manufacture of elements of textile before assembly, or after assembly of the textile. In one aspect, the textile can be treated after assembly of the elements used to form the textile.

In another aspect, the manufacturing of the textile, for example, can include one or more of the following actions: a) making the textile (e.g., a rolled good), b) treating a portion or all of the textile with the aqueous solution to prepare the treated textile (e.g., a treated rolled good), c) cutting the textile into individual elements, and d) assembling individual elements (e.g., sew or weld them together), treated and/or untreated elements, to form an article of apparel, where the order of b) and c) can be switched. In an aspect, a single party can perform each of these actions to manufacture the textile. In another aspect, two or more can independently perform these actions to manufacture the textile.

EXAMPLES

For the following examples, unless otherwise specified, 100% polyester knit single jersey fabric of 145 grams per square meters, dyed black and ready for finish, was used for the treatment.

Formulation of the Aqueous Solution and Method of Treating the Textile

Treatment Solution A, containing the following chemicals was prepared: 2 wt % trehalose, 2 wt % sodium hypophosphite, 8 wt % polyacrylic acid (20% solution, MW 2000-10,000), and 3 wt % polyethylene glycol ester. The solution pH was adjusted with acid to 4-5. Fabric was dipped and padded in the solution and run between 2 rollers to achieve a 70-80 wt % wet pickup, then dried and cured at 140° C. for 2 minutes.

Testing Procedures for Aldehyde Odor Inhibition

First, a small sample of substrate (2.25 $cm^2$±0.1 $cm^2$) was cut. For the purposes of the testing, the substrate was a polyester knit fabric textile product as described above. The sample was placed in an injection vial, lying flat on the bottom of the vial. The sample was treated with aqueous Treatment Solution A, described above.

8 μL triolein was inserted by injection syringe through the sealing film into the vial flask on the sample. Triolein is used as a test compound as it is a compound which, when oxidized, breaks down into C5-C12 (or C5-C8) aldehydes. In the method, triolein is oxidized in the presence of untreated and treated substrate to evaluate the effect of the treatment on the level of aldehydes detected in the head space of the samples 3 μL of the internal standard component trimethylsilanol was then inserted onto the vial flask wall, taking care to avoid contact with the sample and the odor component.

The vial flask was kept at 180° C. for 30 minutes using a heating plate with no agitation or stirring of the testing gas. After the 30 minutes of heating, a gastight syringe was inserted vertically into the center of the sealing film and 1 mL of odor testing gas sampled from inside the vial flask with the syringe.

The concentration of the testing gas was then sampled using gas-chromatography-mass spectrometry (GC-MS). The testing gas obtained from the vial flask was injected into the column of the GC, and the concentration of odor component chemicals were then detected by mass spectrometer. The peak area value of the MS were obtained as the value proportional to the concentration of the testing gas.

Calculation of Odor Reduction Rate

The following formula was used to calculate the rate of reduction of odor compounds from the samples:

$$ORR = \frac{(Sb - Sm)}{Sb} \times 100$$

Where ORR is the odor reduction rate, as a percentage; Sm is the target C5-C12 aldehyde odor peak ratio of Mass Spectrum of the testing gas for the treated sample; and Sb is the target odor peak ratio of Mass Spectrum of the testing gas for the untreated sample.

To test for durability of the fabric treatment during laundering, all fabrics were washed in hot water (at 60° C.), with a protocol according to AATCC method M6. Results of the Odor Reduction Rate test before and after are shown in Table 1 Treated polyester fabrics showed reduction of C6 to C8 aldehyde generation from triolein oxidation. Even after 25 wash and dry cycles, the treatment demonstrated its durable inhibition effectiveness.

TABLE 1

Aldehyde reduction rates (ORR) of treated polyester fabrics

|  | Before wash | 5 washes | 25 washes |
|---|---|---|---|
| Pentanal | 37.86 | 32.05 | 23.3 |
| Hexanal | 27.07 | 23.04 | 9.5 |
| Heptanal | 31.63 | 33.11 | 16.4 |
| Octanal | 21.41 | 25.56 | 16.7 |
| n-Nonanal | 22.66 | 17.82 | 7.2 |
| 2-Nonenal | 23.37 | 25.67 | 15.78 |
| 2-Decenal | 21.58 | 36.83 | 21.54 |
| 2-Dodecenal | 21.58 | 30.53 | 24.6 |

Aldehyde Odor Analysis of Worn Fabric Samples

Bi-symmetrical t-shirts were made up for field wear trials. The left and right halves of each test t-shirt were formed from separate panels, so that all the fabric on one half of the t-shirt was treated, and all the fabric on the other half was the control fabric (untreated).

Wear testers wore these t-shirts for their daily workouts (4-12+ hours weekly) and washed them afterwards with their regular laundry. After the 25th wear cycle (before the 25th wash), all of the shirts were returned to the lab for analysis. The 25th wash and dry were done in the lab using the same procedure as the fabric testing above. No deodorants, perfumes, softeners, dryer sheets, or bleach were used in the field wear trials.

Ten fabric samples (8 unwashed and 2 washed) were analyzed by SPME-GC×GC-TOFMS using the methods described above. Solid-phase microextraction (SPME) extraction was performed at 30° C. for 24 hours. For the extraction, a divinylbenzene/carboxen/polydimethylsiloxane (PDMS/CAR/DVB) fiber was used as the solid-phase substrate. Analysis was conducted on both the treated and untreated portions of the garment (Table 2). Results are shown in FIGS. 2A-G.

TABLE 2

Sample code name explanations

| Code name | Sample Description |
|---|---|
| 13LUF0 | Garment #1 from subject #1, untreated side of garment ("L" refers to left side), before 25th wash |
| 13RUF6 | Garment #1 from subject #1, treated side of garment ("R" refers to right side, before 25th wash |
| 15LUF0 | Garment #2 from subject #2, untreated side of garment, before 25th wash |
| 15RUF6 | Garment #2 from subject #2, treated side, before 25th wash |
| 17LUF0 | Garment #3 from subject #3, untreated side, before 25th wash |
| 17RUF6 | Garment #3 from subject #3, treated side, before 25th wash |
| 24LUF0 | Garment #4 from subject #4, untreated side, before 25th wash |
| 24RUF6 | Garment #4 from subject #4, treated side, before 25th wash |
| 24LWF0 | Garment #4 from subject #4, untreated side, after 25th wash |
| 24RWF6 | Garment #4 from subject #4, treated side, after 25th wash |

FIG. 2A-G first shows different volatile aldehyde odor profiles/concentrations among individual wear testers.

When wearing garments, different individuals generate and deposit different amounts and types of odor-causing compounds on the garments. This is demonstrated above, as different concentrations of different volatile aldehydes were detected in the garments worn by different test subjects. With test subjects #1, #2, #3 and #4, the treatment was effective in reducing the amount of the more volatile aldehydes (butanal, hexanal, heptanal and octanal) detected on the garments after wear and before washing. With test subjects #1, #3 and #4, the treatment was effective in reducing the amount of the less volatile aldehydes (nonanal, decanal, and undecanal) detected on the garments after wear and before washing. The garments from test subject 4 were also tested after the 25th washing to determine whether or not the treatment affected the ability of laundering to remove volatile aldehydes from the treated side of the garment. After 25 washings, the levels of each of the aldehydes detected on the treated side of the garment were the same as or in some cases somewhat lower than the levels detected on the untreated side of the garment following the 25th washing. This demonstrates that, after repeated laundering, the presence of the treatment did not negatively affect the effectiveness of laundering in removing aldehydes from the garment.

Figure 2C:
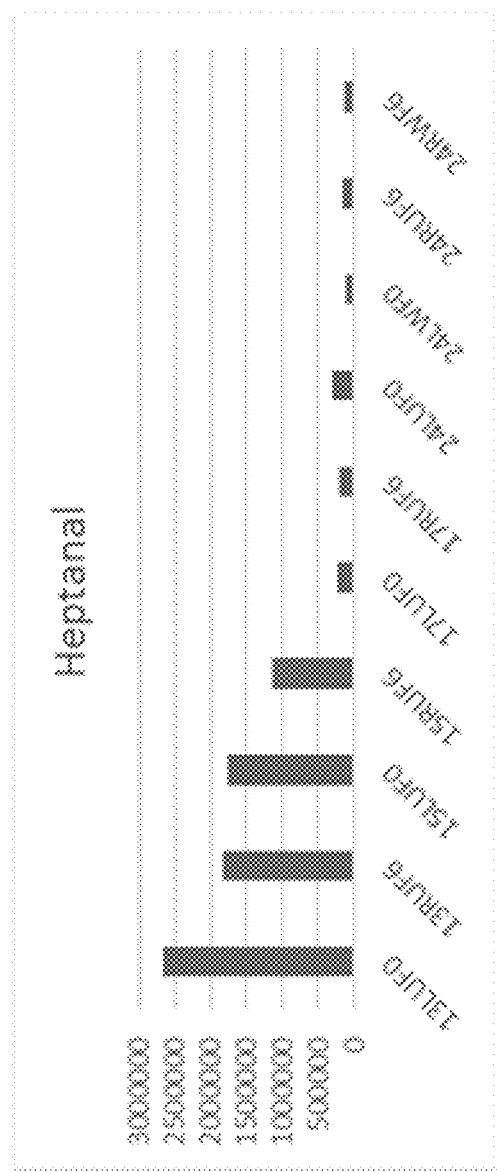
Figure 2D:
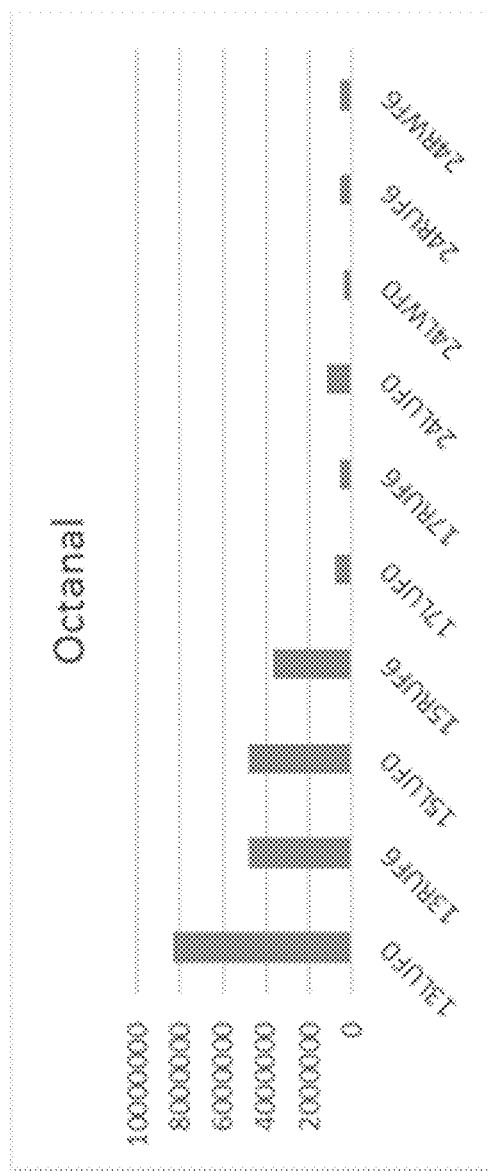
Figure 2E:
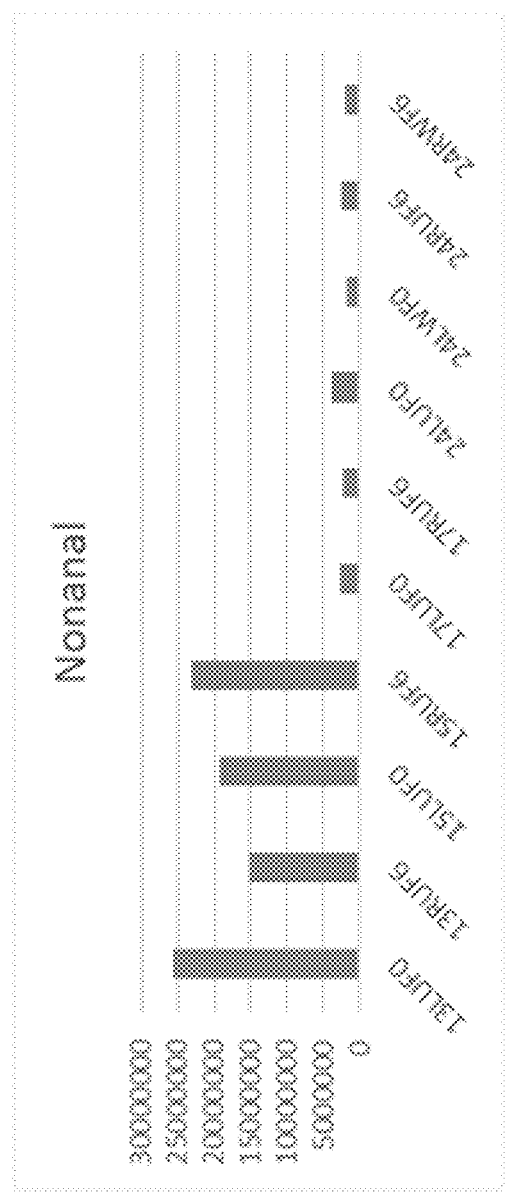
Figure 2F:
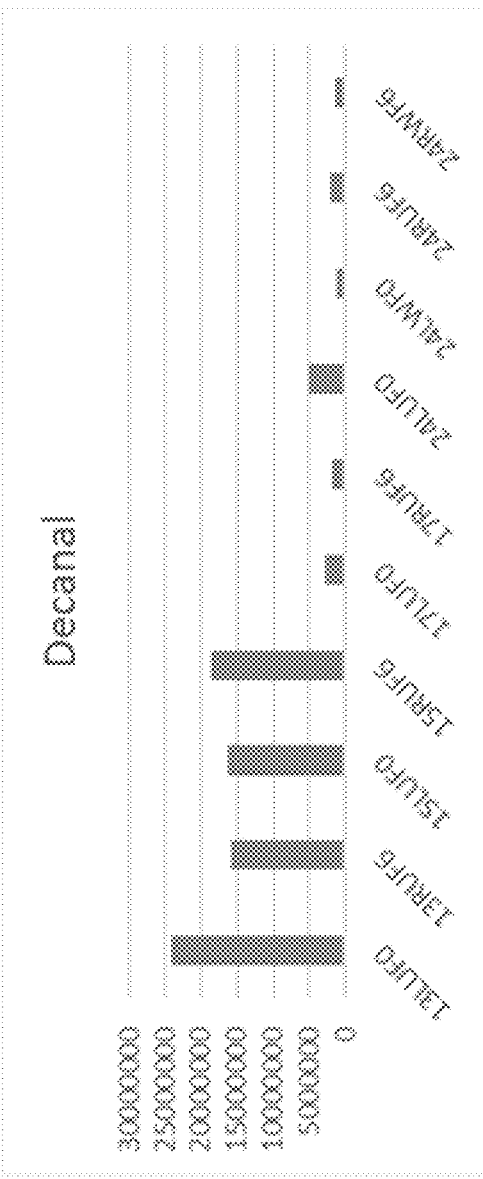
Figure 2G:
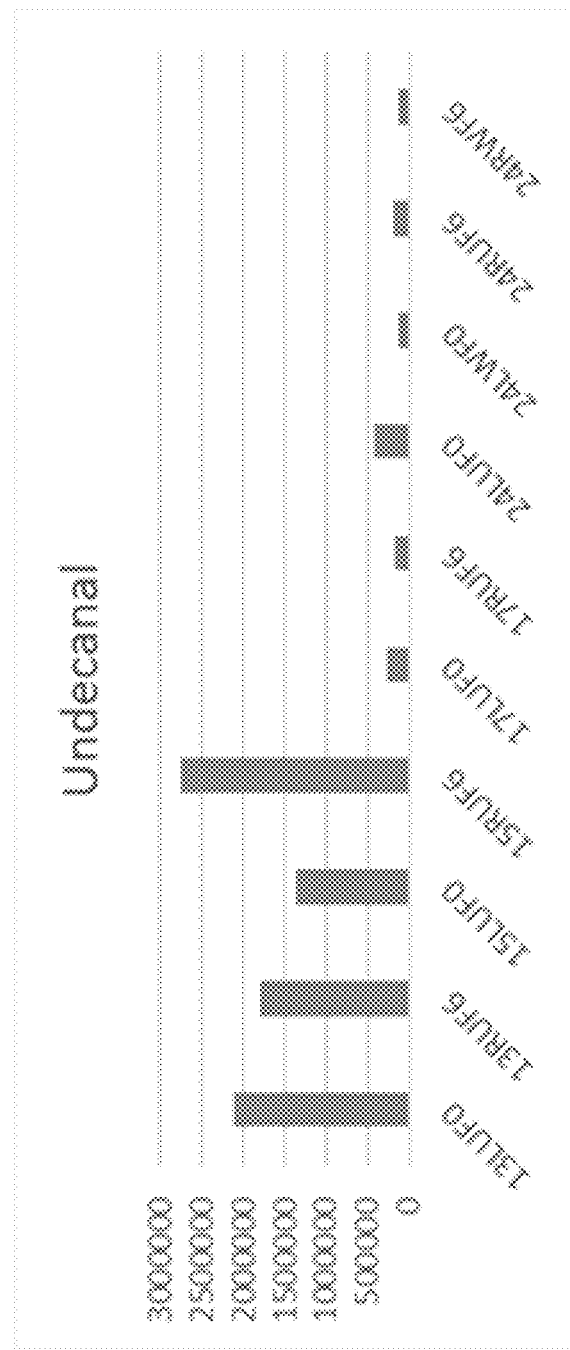

Before the $25^{th}$ wash, all treated fabrics except #3 had lower butanal odor concentration than untreated fabrics (FIG. 2A). For hexanal, heptanal, and octanal C6-C8 saturated aliphatic volatile aldehydes, all treated fabrics showed inhibition effect compared to the untreated control fabrics (FIG. 2B-D). For nonanal, decanal, and undecanal C9-C11 less volatile aliphatic aldehydes, all treated fabrics except #2 demonstrated odor inhibition performance via lower aldehyde concentrations than untreated control fabrics. After the $25^{th}$ wash, most volatile C4-C11 aldehydes were removed by washing and drying.

It should be emphasized that the above-described aspects of the present disclosure are merely possible examples of implementations, and are set forth only for a clear understanding of the principles of the disclosure. Many variations and modifications may be made to the above-described aspects of the disclosure without departing substantially from the spirit and principles of the disclosure. All such modifications and variations are intended to be included herein within the scope of this disclosure.

The present disclosure will be better understood upon review of the following clauses, which should not be confused with the claims.

Clause 1: An aqueous solution comprising: an inhibitor agent and optionally, one or more of the following: a cross-linker, a softener, and an alkali metal salt catalyst, wherein the inhibitor agent functions in one or more of the following ways: as a lipid peroxidation inhibitor, as an aldehyde inhibitor, or as an antioxidant, and wherein the concentration of the inhibitor agent is about 0.01 to less than 10 wt % of the solution.

Clause 2: The aqueous solution of clause 1, wherein the inhibitor agent is selected from the group consisting of: a polysaccharide, an antioxidant, L-ascorbic acid, a modified antioxidative antimicrobial chitosan, and a combination thereof.

Clause 3: The aqueous solution of clause 2, wherein the polysaccharide comprises trehalose or trehalose derivatives.

Clause 4: The aqueous solution of any one of clauses 1-3, wherein the stain release agent is selected from the group consisting of: a carboxymethyl cellulose salt, an oligomeric copolymers of terephthalic acid with ethylene glycol and polyethylene glycol, a carboxy based hydrophilic polymer, and a combination thereof; and wherein the concentration of the stain release agent is about 0.01 to 5 wt % of the solution.

Clause 5: The aqueous solution of any one of clauses 1-4, wherein the cross-linker is selected from the group consisting of: a polycarboxylic acid crosslinking agent, an aldehyde crosslinking agent, a polyisocyanate crosslinking agent, and a combination thereof, wherein the concentration of the cross-linker is about 0.01 to 5 wt % of the solution.

Clause 6: The aqueous solution of clause 5, wherein the polycarboxylic acid crosslinking agent is selected from the group consisting of: polyacrylic acid, a polymaleic acid, a copolymer of acid, a copolymer of maleic acid, fumaric acid, 1,2,3,4-butanetetracarboxylic acid, and a combination thereof.

Clause 7: The aqueous solution of any one of clauses 1-6, wherein the alkali metal salt catalyst is selected from the group consisting of: alkali metal hypophosphites, alkali metal phosphites, alkali metal polyphosphonates, alkali metal phosphates, and alkali metal sulfonates; and wherein the concentration of the alkali metal salt catalyst is about 0.01 to 10 wt % of the solution.

Clause 8: The aqueous solution of clause 7, wherein the alkali metal hypophosphite is sodium hypophosphite.

Clause 9: The aqueous solution of any one of clauses 1-8, wherein the softener is selected from the group consisting of: a silicone, a fatty acid, a fatty acid derivative, an aliphatic glycol ester, an aliphatic phthalate copolymer, a derivative of an aliphatic phthalate copolymer, polyethylene glycol ester, polyethylene terephthalate copolymer, derivatives of polyethylene terephthalate, and a combination thereof; and wherein the concentration of the softener is about 0.01 to 6 weight % of the solution.

Clause 10: The aqueous solution of clause 1, wherein the inhibitor agent is trehalose, wherein the cross-linker is polyacrylic acid, wherein the alkali metal hypophosphite is sodium hypophosphite, wherein the softener is polyethylene glycol ester, wherein the trehalose is at about 0.01 to 10 weight % of the solution and one or more of the following is present: polyacrylic acid is at about 0.01 to 5 weight % of the solution; sodium hypophosphite is at about 0.01 to 10 weight % of the solution; and polyethylene glycol ester is at about 0.01 to 6 weight % of the solution.

Clause 11: A method of treating a substrate, comprising: exposing the substrate to the aqueous solution of any one of clauses 1 to 10; drying the substrate; and curing the substrate to form a treated substrate.

Clause 12: The method of clause 11, wherein the substrate comprises a textile.

Clause 13: An article, comprising: a treated substrate having a surface coating comprising an inhibitor agent.

Clause 14: The article of clause 13, wherein the inhibitor agent is selected from the group consisting of: a polysaccharide, an antioxidant, L-ascorbic acid, and modified antioxidative antimicrobial chitosan, and a combination thereof, wherein the concentration of the inhibitor agent is about 0.01 to less than 25 wt % of the solution.

Clause 15: The article of clause 13, wherein the polysaccharide comprises a trehalose and trehalose derivatives, wherein the concentration of the polysaccharide is about 10 to less than 20 wt % of the solution.

Clause 16: The article of any one of clauses 13-15, wherein the surface coating further comprises a stain release agent that is selected from the group consisting of: carboxymethyl cellulose salt, an oligomeric copolymer of terephthalic acid with ethylene glycol and polyethylene glycol, carboxy based hydrophilic polymer, and a combination thereof.

Clause 17: The article of any one of clauses 13-15, wherein the surface coating further comprises a softener that is selected from the group consisting of: polyethylene glycol ester, polyethylene terephthalate copolymer, derivatives of polyethylene terephthalate, and a combination thereof and wherein the concentration of the softener is about 0.01 to 6 weight % of the solution.

Clause 18: The method or article of any one of clauses 11, 13-15, wherein the treated substrate comprises a textile.

Clause 19: The method or article of clause 18, wherein the textile is an article of apparel or component of apparel.

Clause 20: The method or article of clause 18, wherein the textile is an article of footwear or component of footwear.

Clause 21: The method or articles of clauses 18-20, wherein the textile comprises a PET copolymer.

Clause 22: The aqueous solution or surface coating of any one of clauses 1-9, 11-12, and 13-17, further comprising two or more of the following: a stain release agent, a cross-linker, a softener, and an alkali metal salt catalyst.

Clause 23: The aqueous solution or surface coating of any one of clauses 1-9, 11-12, and 13-17, further comprising three or more of the following: a stain release agent, a cross-linker, a softener, and an alkali metal salt catalyst.

Clause 24: The aqueous solution or surface coating of any one of clauses 1-9, 11-12, and 13-17, further comprising a stain release agent, a cross-linker, an alkali metal salt catalyst, and a softener.

Clause 25: An aqueous solution comprising: a trehalose at about 0.01 to 10 weight % of the solution and one or more of the following: polyacrylic acid at about 0.01 to 5 weight % of the solution; sodium hypophosphite at about 0.01 to 10 weight % of the solution; and polyethylene glycol ester at about 0.01 to 6 weight % of the solution.

Clause 26: The aqueous solution of clause 25, wherein the concentration of the trehalose is about 0.01 to less than 5 wt % of the solution.

Clause 27: The aqueous solution of clause 1, wherein the concentration of the trehalose is about 0.01 to about 4 wt % of the solution.

Clause 28: The aqueous solution of clause 1, wherein the concentration of the trehalose is about 0.01 to 1 wt % of the solution.

Clause 29: The aqueous solution of clause 1, wherein two or more of the following are included in the aqueous solution: a carboxymethyl cellulose salt at about 0.01 to 5 weight % of the solution; polyacrylic acid at about 0.01 to 5 weight % of the solution; sodium hypophosphite at about 0.01 to 10 weight % of the solution; and polyethylene glycol ester at about 0.01 to 6 weight % of the solution.

Clause 30: The aqueous solution of clause 1, wherein three or more of the following are included in the aqueous solution: a carboxymethyl cellulose salt at about 0.01 to 5 weight % of the solution; polyacrylic acid at about 0.01 to 5 weight % of the solution; sodium hypophosphite at about 0.01 to 10 weight % of the solution; and polyethylene glycol ester at about 0.01 to 6 weight % of the solution.

Clause 31: The aqueous solution of clause 1, wherein the aqueous solution includes each of: a carboxymethyl cellulose salt at about 0.01 to 5 weight % of the solution; polyacrylic acid at about 0.01 to 5 weight % of the solution; sodium hypophosphite at about 0.01 to 10 weight % of the solution; and polyethylene glycol ester at about 0.01 to 6 weight % of the solution.

Clause 32: A method of treating a substrate, comprising: exposing the substrate to an aqueous solution of any one of clauses 25 to 31; drying the substrate; and curing the substrate to form a treated substrate.

Clause 33: The method of clause 32, wherein the substrate comprises a textile.

Clause 34: The method of clause 32, wherein the textile is an article of apparel or a component of apparel.

Clause 35: The method of clause 32, wherein the textile is an article of footwear or a component of footwear.

Clause 36: The method of clause 33, wherein the textile comprises a polyester-polyurethane copolymer.

Clause 37: The method of clause 32, further comprising making a product including the treated substrate.

Clause 38: A substrate, comprising: a treated substrate having a surface coating comprising trehalose and one or more of the following: polyacrylic acid, sodium hypophosphite, and polyethylene glycol ester.

Clause 39: The substrate of clause 38, wherein the treated substrate comprises a textile.

Clause 40: The substrate of clause 39, wherein the treated substrate is an article of apparel or a component of apparel.

Clause 41: The substrate of clause 40, wherein the treated substrate comprises a polyester-polyurethane copolymer.

Clause 42: The substrate of clause 39, wherein the treated substrate is an article of footwear or a component of footwear.

Clause 43: The substrate of clause 42, wherein the treated substrate comprises a polyester-polyurethane copolymer.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an aspect, the term "about" can include traditional rounding according to significant figures of the numerical value. In addition, the phrase "about 'x' to 'y'" includes "about 'x' to about 'y'".

Many variations and modifications may be made to the above-described aspects. All such modifications and variations are intended to be included herein within the scope of this disclosure and protected by the following claims.

I claim:

1. An article of apparel with anti-odor properties, comprising:
   a plurality of polyester fibers or yarns comprising a durable surface coating, wherein the durable surface coating comprises an aldehyde inhibitor configured to inhibit generation of volatile aldehydes on a treated article of apparel, and a cross-linker, wherein the aldehyde inhibitor comprises a polysaccharide that is covalently bonded to the plurality of polyester fibers or yarns through the cross-linker.

2. The article of apparel of claim 1, wherein the cross-linker is selected from the group consisting of: a polycarboxylic acid crosslinking agent, an aldehyde crosslinking agent, a polyisocyanate crosslinking agent, and a combination thereof.

3. The article of apparel of claim 1, wherein the plurality of polyester fibers or yarns comprise polyethylene terephthalate fibers or yarns.

4. The article of apparel of claim 1, wherein the durable surface coating comprises one or more of the following: polyacrylic acid, sodium hypophosphite, and polyethylene glycol ester.

5. The article of apparel of claim 1, wherein, after exposing the treated article of apparel to 25 wear, wash and dry cycles, the durable surface coating remains effective in inhibiting generation of volatile aldehydes on the treated article of apparel.

6. The article of apparel of claim 1, wherein the durable surface coating is the product of exposing an untreated article of apparel to an aqueous solution comprising the aldehyde inhibitor and the cross-linker, drying the exposed article of apparel, and curing the exposed article of apparel to activate the cross-linker and cross-link the durable surface coating, forming the treated article of apparel.

7. The article of apparel of claim 1, wherein the aldehyde inhibitor comprises trehalose.

8. The article of apparel of claim 1, wherein the durable surface coating further comprises one or more of a stain release agent, a softener, and an alkali metal salt catalyst.

9. The article of apparel of claim 8, wherein the stain release agent is selected from the group consisting of: carboxymethyl cellulose salt, an oligomeric copolymer of terephthalic acid with ethylene glycol and polyethylene glycol, carboxy based hydrophilic polymer, and a combination thereof.

10. The article of apparel of claim 8, wherein the softener is selected from the group consisting of: polyethylene glycol ester, polyethylene terephthalate copolymer, derivatives of polyethylene terephthalate, and a combination thereof.

11. The article of apparel of claim 8, wherein the alkali metal salt catalyst is selected from the group consisting of: alkali metal hypophosphites, alkali metal phosphites, alkali metal polyphosphonates, alkali metal phosphates, and alkali metal sulfonates.

12. The article of apparel of claim 1, wherein the durable surface coating is configured to cure at a temperature of about 120° C. to about 160° C.

13. An article of apparel with anti-odor properties, comprising:
    a plurality of polyester fibers or yarns, comprising polyethylene terephthalate fibers or yarns, wherein the plurality of polyester fibers or yarns comprises a durable surface coating, wherein the durable surface coating is uniformly distributed throughout an article of apparel thickness, the durable surface coating comprising a cross-linker and an aldehyde inhibitor, wherein the aldehyde inhibitor comprises a polymeric composition, wherein the durable surface coating is configured to inhibit generation of volatile aldehydes on the article of apparel during or following wear, and wherein the aldehyde inhibitor is covalently bonded to the at least one of the polyethylene terephthalate fibers or yarns through the cross-linker.

14. The article of apparel of claim 13, wherein the durable surface coating further comprises one or more of the following: a stain release agent, a softener, and an alkali metal salt catalyst.

15. The article of apparel of claim 13, wherein the cross-linker is selected from the group consisting of: a polycarboxylic acid crosslinking agent, an aldehyde crosslinking agent, a polyisocyanate crosslinking agent, and a combination thereof.

16. The article of apparel of claim 13, wherein the durable surface coating is configured to cure at a temperature of about 120° C. to about 160° C.

17. An article of apparel with anti-odor properties, comprising:
 a plurality of polyester fibers or yarns comprising
 a durable surface coating configured to remain in the article of apparel for at least 25 wear, wash and dry cycles, and wherein the durable surface coating comprises an aldehyde inhibitor configured to inhibit generation of volatile aldehydes on a treated article of apparel, and a cross-linker, wherein the aldehyde inhibitor is covalently bonded to the plurality of polyester fibers or yarns through the cross-linker.

18. The article of apparel of claim 17, wherein the cross-linker is selected from the group consisting of: a polycarboxylic acid crosslinking agent, an aldehyde crosslinking agent, a polyisocyanate crosslinking agent, and a combination thereof.

19. The article of apparel of claim 17, wherein the aldehyde inhibitor is bonded to the plurality of polyester fibers or yarns.

20. The article of apparel of claim 17, wherein the durable surface coating further comprises one or more of a stain release agent, a softener, and an alkali metal salt catalyst.

21. The article of apparel of claim 1, wherein the aldehyde inhibitor has an odor reduction rate of at least 7.2 percent after 25 wash cycles.

* * * * *